United States Patent
Takai et al.

(10) Patent No.: US 8,581,016 B2
(45) Date of Patent: *Nov. 12, 2013

(54) PROCESS FOR PRODUCING ALKYLATED AROMATIC COMPOUND AND PROCESS FOR PRODUCING PHENOL

(75) Inventors: Toshihiro Takai, Nishinomiya (JP); Michiaki Umeno, Chiba (JP); Shinobu Aoki, Ichihara (JP); Terunori Fujita, Yokohama (JP); Tsuneyuki Ohkubo, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 818 days.

This patent is subject to a terminal disclaimer.

(21) Appl. No.: 12/312,647

(22) PCT Filed: Nov. 1, 2007

(86) PCT No.: PCT/JP2007/071290
§ 371 (c)(1),
(2), (4) Date: Jun. 26, 2009

(87) PCT Pub. No.: WO2008/062644
PCT Pub. Date: May 29, 2008

(65) Prior Publication Data
US 2010/0022812 A1    Jan. 28, 2010

(30) Foreign Application Priority Data

Nov. 21, 2006  (JP) ................................ 2006-314603
Feb. 27, 2007  (JP) ................................ 2007-047443

(51) Int. Cl.
*C07C 1/207*    (2006.01)

(52) U.S. Cl.
USPC ............................ 585/469; 568/715; 568/716

(58) Field of Classification Search
USPC .................................... 585/469; 568/715, 716
See application file for complete search history.

(56) References Cited

U.S. PATENT DOCUMENTS

| | | | |
|---|---|---|---|
| 5,015,786 A | 5/1991 | Araki et al. | |
| 5,017,729 A | 5/1991 | Fukuhara et al. | |
| 6,225,477 B1 | 5/2001 | Ernst et al. | |
| 6,762,324 B2 | 7/2004 | Ding | |
| 6,841,704 B2 | 1/2005 | Sakuth et al. | |
| 6,878,849 B2 | 4/2005 | Ding | |
| 6,903,046 B2 | 6/2005 | Ding | |
| 6,924,395 B2 | 8/2005 | Ding | |
| 6,939,995 B2 | 9/2005 | Chewter et al. | |
| 7,524,788 B2 | 4/2009 | Girotti et al. | |
| 2004/0162448 A1 | 8/2004 | Yang et al. | |

FOREIGN PATENT DOCUMENTS

| | | |
|---|---|---|
| CN | 1246807 A | 3/2000 |
| CN | 1454713 A | 11/2003 |
| EP | 1 069 099 A1 | 1/2001 |
| JP | 57-91972 A | 6/1982 |
| JP | 2-174737 A | 7/1990 |
| JP | 2-231442 A | 9/1990 |
| JP | 11-35497 A | 2/1999 |
| JP | 2003-523985 A | 8/2003 |
| JP | 2004-536147 A | 12/2004 |
| JP | 2005-513116 A | 5/2005 |
| WO | WO 03/053892 A1 | 7/2003 |

OTHER PUBLICATIONS

Barman et al., "Kinetics of Reductive Isopropylation of Benzene with Acetone over Nano-Copper Chromite-Loaded H-Mordenite," Industrial & Engineering Chemistry Research, Apr. 14, 2006, vol. 45, No. 10, pp. 3481-3487.
European Search Report mailed Nov. 11, 2009 in European Application No. 07831024.0 (6 pgs.).
Office Action in CN Appln No. 200780042839 dated Mar. 12, 2012.

*Primary Examiner* — Thuan D Dang
(74) *Attorney, Agent, or Firm* — Foley & Lardner LLP

(57) ABSTRACT

The present invention provides an industrially practical process where a ketone and an aromatic compound are directly reacted to obtain a corresponding alkylated aromatic compound in a single reaction step. The process for producing an alkylated aromatic compound is characterized in that it comprises reacting an aromatic compound, a ketone and hydrogen in the presence of a solid acid substance and a catalyst composition comprising at least one metal selected from the group consisting of Co, Re, Ni and a platinum group metal.

12 Claims, No Drawings

US 8,581,016 B2

PROCESS FOR PRODUCING ALKYLATED AROMATIC COMPOUND AND PROCESS FOR PRODUCING PHENOL

TECHNICAL FIELD

The present invention relates to a process for allowing an aromatic compound to react with a ketone and hydrogen to produce a corresponding alkylated aromatic compound by, and to a process for producing a phenol wherein the above process is performed in a step. More specifically, it relates to a process for producing an alkylated aromatic compound by reacting a ketone, an aromatic compound and hydrogen using a specific catalyst in a single reaction step, and to a process for producing a phenol wherein the above process is performed in a step.

BACKGROUND OF THE INVENTION

A process for producing cumene by reacting benzene and propylene, a process for producing cumene hydroperoxide by oxidizing cumene, and a process for producing phenol and acetone by acid decomposing cumene hydroperoxide are each known. A process in which these reactions are combined is a production process for a phenol generally called as a cumene method, and is a main process for producing a phenol.

The cumene method has a property that acetone is produced simultaneously. Although the property becomes merits when acetone is simultaneously desired, when acetone is obtained in an excessive amount with respect to the demand thereof, the cost difference with propylene which is a raw material acts disadvantageously to lead to a bad economic efficiency. Therefore, in order to lead the cost difference between an olefin which is a raw material and a ketone which is co-produced to advantageousness, proposed is, for example, a process for simultaneously producing phenol and methylethyl ketone by oxidizing and acid decomposing secondary butyl benzene obtainable from n-butene and benzene (referred to Patent documents 1 and 2). In this process, since the selectivity of secondary butylbenzene hydroperoxide, which is an aimed product by oxidation of secondary butyl benzene, is only about 80% while acetophenone is incidentally produced in an amount of 15% or more, the yield of this process as a phenol production process does not reach to that of the cumene method.

Furthermore, a process for obtaining phenol and cyclohexanone by oxidizing and acid decomposing cyclohexylbenzene obtainable from cyclohexene and benzene is also proposed. In this process, since phenol is obtained by dehydrogenating resulting cyclohexanone, the by-production of a ketone can be avoided formally. In the oxidation reaction of cyclohexylbenzene, however, the yield of aimed cyclohexylbenzenehydroperoxide is low and the industrial value thereof is low.

Under the circumstances, for the cumene method having the highest yields of oxidation and acid decomposition, in order to avoid the defect of acetone incidentally produced with propylene which is a raw material while keeping the superiority, methods for reusing the acetone which is by-produced using various methods are proposed.

Acetone is easily convertible into isopropanol by hydrogenation. The process where this isopropanol is dehydrated to prepare propylene and then it is allowed to react with benzene to obtain cumene. Namely, a process of reusing acetone as a raw material for the cumene method is proposed (referred to Patent document 3). This process, however, has a problem of having two additional steps of hydrogenation step and dehydration step.

Consequently, processes of obtaining cumene by directly allowing isopropanol obtained by hydrogenation of acetone to react with benzene are proposed (referred to Patent documents 4 to 6). Particularly, the patent document 6 discloses a process of preparing isopropanol from acetone by-produced and producing phenol by using cumene obtained by allowing it to react with benzene. The process, however, also has an additional hydrogenation step as compared with the original cumene method.

On the other hand, as a process of reusing by-produced acetone without adding any steps to the conventional cumene method, namely a process of directly react acetone, benzene and hydrogen, a process of allowing them to react in the co-presence of hydrogen using a catalyst system which comprises a solid acid substance and a Cu compound is disclosed (Patent document 7). However, the process described in the patent document 7 has a tendency that propane is by-produced in the preparation of cumene.

Patent document 1: JP-A-S57-91972
Patent document 2: US-A-2004-0162448 specification
Patent document 3: JP-A-H2-174737
Patent document 4: JP-A-H2-231442
Patent document 5: JP-A-H11-35497
Patent document 6: JP-A-2003-523985
Patent document 7: JP-A-2005-513116

DISCLOSURE OF THE INVENTION

Object of the Invention

The present invention aims to provide a new process for producing an alkylated aromatic compound which can establish a method industrially practical and which is for obtaining cumene by directly reacting acetone, benzene and hydrogen. The present invention aims to provide a process for producing a phenol in a step of which the above process is performed and which does not involve any additional steps as compared with the conventional cumene method.

Means for Solving the Object

The present inventors have been earnestly studied for solving the above objects and found that, by using a solid acid substance and a catalyst composition containing a specific metal as catalysts with a ketone such as acetone, an aromatic compound such as benzene and hydrogen as starting materials, a corresponding alkylated aromatic compound such as cumene can be obtained with a high yield in a single reaction step.

That is to say, the process for producing an alkylated aromatic compound according to the present invention is characterized in that it comprises reacting an aromatic compound, a ketone and hydrogen in the presence of a solid acid substance and a catalyst composition containing at least one metal selected from the group consisting of Co, Re, Ni and a platinum group metal.

The metal is preferably at least one metal selected from the group consisting of Co, Re, Ni, Pt and Pd, more preferably at least one metal selected from the group consisting of Co, Re and Ni.

The aromatic compound is preferably benzene, and the ketone is preferably acetone.

The solid acid substance is preferably a zeolite compound, more preferably a zeolite compound having 10- to 16-membered oxygen ring pores, particularly preferably a zeolite compound having 10- or 12-membered oxygen ring pores.

Specifically, the solid acid substance is preferably at least one zeolite compound selected from the group consisting of β zeolite, MCM-22 zeolite, mordenite, ZSM-5 zeolite, ZSM-12 zeolite and Y type zeolite, more preferably at least one zeolite compound selected from the group consisting of β zeolite and MCM-22 zeolite.

The catalyst composition preferably comprises a carrier supporting at least one metal selected from the group consisting of Co, Re, Ni, Pt and Pd, more preferably the metal is at least one metal selected from the group consisting of Co, Re and Ni.

The process for producing a phenol according to the present invention comprises:

(a) a step of converting cumene into cumene hydroperoxide by oxidation, (b) a step of synthesizing phenol and acetone by acid decomposing the cumene hydroperoxide, (c) a step of synthesizing cumene by reacting the acetone generated in the step (b) with hydrogen and benzene, and (d) a step of circulating the cumene obtained in the step (c) into the step (a).

It is characterized in that the step (c) is carried out in accordance with the above process for producing an alkylated aromatic compound.

Advantages of the Invention

According to the process for producing an alkylated aromatic compound of the present invention, an alkylated aromatic compound such as cumene can be obtained by an industrially practical method with a ketone such as acetone, an aromatic compound such as benzene and hydrogen as starting materials in a single reaction step. Further, in the process for producing a phenol in a step of which the process for producing an alkylated aromatic compound is performed, by-produced acetone can be reused without adding the number of step in the conventional cumene method. Furthermore, it is an epochal technique such that the cumene obtained by the process for producing an alkylated aromatic compound has no problem in quality as compared with cumene obtained from propylene or isopropanol and benzene. It the process can advantageously produce phenol from the viewpoints of process and economy.

PREFERRED EMBODIMENTS OF THE INVENTION

The process for producing an alkylated aromatic compound according to the present invention is characterized in that it comprise reacting an aromatic compound, a ketone and hydrogen in the presence of a solid acid substance and a catalyst composition comprising at least one metal selected from the group consisting of Co, Re, Ni and a platinum group metal.

In the present invention, the two components of the solid acid substance and the metal-containing catalyst composition should be used and there is particularly no limitation on the use method thereof. The solid acid substance as an acid catalyst component and the catalyst composition containing the metal may be mixed physically in a level of catalytic particles with a centimeter size. Both of them may be pulverized and mixed followed by being molded anew into catalytic particles with a centimeter size. Moreover, the catalyst composition containing the metal may be supported on the solid acid substance acting as an acid catalyst as a carrier. Conversely, the solid acid substance may be supported on the catalyst composition containing the metal as a carrier.

The solid acid substance used in the present invention is a catalyst having a function as an acid and should be those being generally called as a solid acid. Zeolite compound, silica alumina, alumina, sulfuric acid ion-supporting zirconia $WO_3$-supporting zirconia and the like can be used.

The zeolite compound, which is an inorganic crystalline porous compound mainly constituted by silicon and aluminum, is a suitable alkylation catalyst from the viewpoint of heat resistance and selectivity of an aimed alkylated aromatic compound. A suitable zeolite compound varies depending on an aromatic compound used as a raw material and the molecular diameter of an aimed alkylated aromatic compound.

For example, when cumene is prepared as an alkylated aromatic compound by using benzene as an aromatic compound and acetone as a ketone, it is preferred to use a zeolite compound having 10- to 16-membered oxygen ring pores as the zeolite compound.

Examples of the zeolite compound having 10- to 16-membered oxygen ring pores include ferrierite, heulandite, ZSM-5 zeolite, ZSM-11 zeolite, ZSM-12 zeolite, NU-87 zeolite, theta 1 zeolite, weinebeneite, X type zeolite, Y type zeolite, USY type zeolite, mordenite, de-aluminized mordenite, β-zeolite, MCM-22 zeolite, MCM-36 zeolite, MCM-56 zeolite, gmelinite, offretite, cloverite, VPI-5 zeolite and UTD-1 zeolite.

Of these zeolite compounds, those having pores similar to the molecular diameter of cumene are preferable. It is more preferred to use zeolite compounds having 10- or 12-membered oxygen ring pores. Examples of the zeolite compounds having 10- or 12-membered oxygen ring pores include Y type zeolite, USY type zeolite, mordenite, de-aluminized mordenite, β-zeolite, MCM-22 zeolite, MCM-56 zeolite, ZSM-12 zeolite and ZSM-5 zeolite. Among them, from the viewpoint of cumene selectivity, β-zeolite, MCM-22 zeolite, mordenite, ZSM-5 zeolite, ZSM-12 zeolite and Y type zeolite are more preferred, and β-zeolite and MCM-22 zeolite are particularly preferred.

The composition ratio of silicon to aluminum (silicon/aluminum) in these zeolite compounds should be in the range of 2/1 to 200/1, and from the viewpoint of activity and heat stability, it is preferably in the range of 5/1 to 100/1. Furthermore, it is also possible to use so-called isomorphically substituted zeolite compounds obtainable by substituting aluminum atom contained in the zeolite skeleton with a metal other than aluminum, such as Ga, Ti, Fe, Mn or B.

The solid acid substance has a shape which is not particularly limited and may have any one of spherical, cylindrical, extruded and pulverized shapes. Further, a particle size of it may be selected from the range of 0.01 mm to 100 mm depending on the size of a reactor.

The solid acid substance may be used singly and two or more kinds thereof may be used.

The metal-containing catalyst composition used in the present invention is a catalyst composition containing at least one metal selected from the group consisting of Co, Re, Ni and platinum group metals, preferably at least one metal selected from the group consisting of Co, Re, Ni, Pt and Pd, more preferably at least one metal selected from the group consisting of Co, Re and Ni.

Mention may be made of those containing at least one metal selected from the group consisting of Co, Re, Ni and platinum group metals as it is, and those containing at least one such metal as a metal compound, as the metal-containing catalyst composition. Examples are a metal oxide such as $CoO$, $Co_2O_3$, $ReO_2$, $Re_2O_7$, $NiO$, $PdO$, $Rh_2O_3$ and $RuO_2$; a metal chloride such as $CoCl_2$, $ReCl_3$, $NiCl_2$, $PdCl_2$, $RhCl_3$ and $RuCl_3$; and those containing in a cluster metal form such as Ru—Rh or Ru—Pt.

Other examples include cobalt(II) nitrate, cobalt(II) acetate, cobalt(II) sulfate, cobalt(II) sulfide, diammonium cobalt(II) sulfate, cobalt hydroxide, cobalt (II) bromide, basic cobalt(II) carbonate, cobalt hexammine chloride, cobalt(II) phosphate, cobalt sponge, cobalt powder, Raney cobalt, cobalt(II) benzoate, cobalt naphthenate, sodium hexanitrocobaltate (III), chlorophthalocyaninato cobalt(II), tetra-t-butylphthalocyaninato cobalt(II), tetra-aminochlorophthalocyaninato cobalt (II), tetra-carboxyphthalocyaninato cobalt (II), 2,3,7,8,12,13,17,18-octaethylporphyrinato cobalt(II), cobalt(II) 2-ethylhexanoate, 5,10,15,20-tetraphenylporphyrinato cobalt(II), cobalt(II) gluconate, sodium dicyanao(phthalocyaninato) cobalt (III), dibromo-bis(triphenylphosphine) cobalt and cobalt(II) stearate.

The catalyst composition containing at least one metal selected from the group consisting of Co, Re, Ni and platinum group metals is used in the present invention. Furthermore, it is preferable that the metal is at least one metal selected from the group consisting of Co, Re, Ni, Pt and Pd because the by-production of alkene is decreased in producing an alkylated aromatic compound. That is to say, in producing cumene by reacting benzene, acetone and hydrogen, hydrocarbons such as propane are occasionally by-produced. However, the use of the catalyst composition containing at least one metal selected from the group consisting of Co, Re, Ni, Pt and Pd decreases the by-production of hydrocarbons such as propane.

The metal is preferably at least one metal selected from the group consisting of Co, Re and Ni because the by-production of cyclic olefins is decreased in producing the alkylated aromatic compound. That is to say, for example, cyclohexane is occasionally by-produced in producing cumene by reacting benzene, acetone and hydrogen. However, use of the catalyst composition containing at least one metal selected from the group consisting of Co, Re and Ni decreases the by-production of cyclohexane.

The catalyst composition containing at least one metal selected from the group consisting of Co, Re, Ni and a platinum group metal is not particularly limited as long as it has capability of hydrogenating a carbonyl functional group to alcohol. So-called hydrogenation catalysts which are commercially available can be used as they are, and those supported on various carriers and the like are available in the market.

As the carrier, for example, silica, alumina, silica alumina, titania, magnesia, silica magnesia, zirconia, carbon, acid clay and diatomaceous earth can be used. Among them, it is preferred to select at least one of silica, alumina, silica alumina, titania, magnesia, silica magnesia, zirconia and carbon.

Examples of the commercially available catalyst compositions include Co on alumina catalyst, Co on silica catalyst, Co on carbon catalyst, 5% Re carbon catalyst, 5% Re alumina catalyst, nickel on silica alumina catalyst, 5% Pd carbon catalyst, Lindlar catalyst (obtainable by adding Pb to Pd carbon catalyst), 5% Pt carbon catalyst, 0.5% Pt sulfided carbon catalyst, 5% Rh alumina catalyst and 5% Ru alumina catalyst. It is also possible to use those obtainable by varying the supported amount to 1% or 0.5%. In these catalysts, it is preferable that at least one metal selected from the group consisting of Co, Re and Ni is contained from the viewpoint of the yield of an aimed compound.

These catalyst compositions containing the metal may be used singly and two or more kinds thereof may be used.

Furthermore, when a metal salt such as $PbSO_4$, $FeCl_2$ or $SnCl_2$, an alkali metal or an alkali metal salt such as K or Na, $BaSO_4$ or the like is added to these catalyst compositions containing the metal, the activity and the selectivity are improved in a certain case. These can be added in accordance with the necessity.

The catalyst composition containing the metal has a shape which is not particularly limited and may have any one of spherical, cylindrical, extruded and pulverized shapes. Further, a particle size of it may be selected from the range of 0.01 mm to 100 mm depending on the size of a reactor.

These catalyst compositions containing the metal may be supported on the above-described solid acid substance. Specifically, it can be supported on the solid acid substance by a method of impregnating the solid acid substance with a nitrate aqueous solution of at least one metal selected from the group consisting of Co, Re, Ni and a platinum group metal and calcining, a method of making these into a complex bonded with an organic molecule which is called as a ligand in order to make them soluble in an organic solvent, adding them to the organic solvent to prepare a solution, and then impregnating the solid acid substance with the solution followed by calcining, a method of depositing due to that some of the complexes vaporize in a vacuum.

Moreover, in preparing the solid acid substance from the corresponding metal salt, it is possible to employ a coprecipitation method where carrier synthesis and support of the metal-containing catalyst composition are simultaneously carried out by coexisting of a salt of at least one metal selected from the group consisting of Co, Re, Ni and a platinum group metal which is to be a hydrogenation catalyst.

In the present invention, compounds having 6 to 20 carbon atoms can be exemplified as examples of the aromatic compound. For example, they include benzene homologues such as benzene, toluene and xylene, and their substituent derivatives; and naphthalene homologues such as naphthalene and methyl naphthalene, and their substituent derivatives. Examples of ketone are compounds having 3 to 20 carbon atoms, and those symmetric and asymmetric can be used.

Examples of the group bonding to a carbonyl group include an alkyl group and an aryl group. Specifically, mention may be made of acetone, methylethyl ketone, acetophenone and the like.

Of these, the reaction for producing cumene by using benzene as the aromatic compound and acetone as the ketone is industrially most important. In this case, the molar ratio of benzenetoacetone (benzene/acetone) is preferably 1 to 20. When it is lower than that range, the productions of diisopropyl benzene and triisopropyl benzene are apt to be increased. In the process of cumene, diisopropyl benzene and triisopropyl benzene can be returned to cumene by trans-alkylation with benzene. However, the trans-alkylation is uneconomical because the reaction temperature is high, and when the amounts of diisopropyl benzene and triisopropyl benzene are too large, the steam cost is increased. While, when it is over the above range, it is uneconomical because a distillation column is loaded in recovering the excess benzene in the post step of the reactor.

The reaction of the aromatic compound and ketone according to the present invention is characterized by being carried out in the presence of hydrogen. The hydrogen used herein may be a hydrogen gas in a molecule state or a hydrocarbon such as cyclohexane which generates hydrogen in the reaction condition. When acetone, benzene and hydrogen are reacted, the hydrogen should be equimolecular or larger than acetone in principle. From the viewpoint of recovering with separation, the preferable range is 1 to 10 times mole, more preferably 1 to 5 times mole based on acetone. When it is desired that the convert ratio of acetone be depressed to 100% or less, it can be met by decreasing the amount of hydrogen used from 1 time mole. Furthermore, hydrogen for feeding in the reaction of the present invention is reacted with oxygen atom of acetone to be made into water, and can be taken out together with cumene from the outlet of the reactor. Moreover, hydrogen in an amount more than or equal to the equivalent amount with acetone is not used essentially as long as undesirable side reaction does not proceed.

When hydrogen gas is added to the reaction, it is generally fed continuously. However, it is not particularly limited this method. It is possible to employ intermittent feeding that at the beginning of the reaction, hydrogen is added, and then the hydrogen feeding is stopped during the reaction and after a certain time, hydrogen is fed again. Further, in the liquid phase reaction, hydrogen gas may be dissolved in a solvent and fed. Moreover, in the recycle process, hydrogen gas recovered together with light boiling fractions from the top of a tower may be fed. In general, the pressure of hydrogen to be added is the same as the pressure of the reactor, but it may be properly changed according to the method for feeding hydrogen.

In carrying out the present reaction, the methods and conditions thereof do not particularly have limitations. For example, it is possible to employ the following conditions and methods.

The contact of acetone, benzene and hydrogen gas which are reaction raw materials is conducted in any one of gas-liquid counter current and gas-liquid parallel current, in any one liquid-gas direction of liquid descending—gas ascending, liquid ascending—gas descending, liquid-gas ascending and liquid-gas descending.

Although the reaction temperature is also not particularly limited in the present invention, it is preferably in the range of 50 to 300° C., more preferably 60 to 200° C. In general, the pressure range for carrying out is preferably 0.1 to 500 atm, more preferably 0.5 to 100 atm.

Furthermore, the catalyst amount used in carrying out the present invention is not particularly limited. For example, in the reaction using a fixed bed flow reactor, the catalyst amount, as represented by a value determined by dividing the feeding amount (weight) of raw materials (ketone+aromatic compound) per hour by the weight of catalyst, namely WHSV, is preferably in the range of 0.1 to 200/h, more preferably 0.2 to 100/h.

The weight ratio of the solid acid substance to the catalyst composition containing at least one metal selected from the group consisting of Co, Re, Ni and a platinum group metal is not particularly limited. In general, the solid acid substance the metal-containing catalyst composition (the weight ratio) is 1:0.01 to 1:100, preferably 1:0.05 to 1:50. When the weight ratio of solid acid substance is too small, it is not economical because the alkylation reaction is not sufficiently carried out to decrease the yield of the alkylated aromatic compound such as cumene. Moreover, when the weight ratio of the solid acid substance is too large, it is also not economical because the conversion rate of acetone is decreased.

In the process for producing the alkylated aromatic compound of the present invention, it is considered that after a ketone is hydrogenated to generate alcohol by the function of the metal-containing catalyst composition, the alcohol and the aromatic compound are alkylated by the function of the solid acid substance and thereby made into the alkylated aromatic compound. That is to say, it is considered that hydrogenation and alkylation take place step by step in the production process of the present invention.

When the fixed bed reaction is employed for the reaction form of the present invention, the filling method of the solid acid substance and the metal-containing catalyst composition occasionally affects the reaction result largely. As described above, it is considered that hydrogenation and alkylation take place step by step in the present invention. Therefore, filling of catalyst seeds proper for each step of the reaction in order is a preferable filling method from the viewpoints that the catalyst is used efficiently and undesirable side reactions are controlled.

In particular, when the hydrogen pressure or the temperature is increased in order to increase the reaction rate, the occurrence of undesirable side reactions which are not found at a low hydrogen pressure or at a low reaction temperature is common in general chemical reactions. Such a case has a possibility that the method of filling the catalyst largely affects the reaction results.

Examples of the method of filling the catalyst seeds proper for each step of the reaction in order are as follows:

(1) A method of mixing the solid acid substance and the metal-containing catalyst composition, and filling them.

(2) A method of filling such that a layer of the metal-containing catalyst composition (upper-stream side) and a layer of the solid acid substance (lower-stream side) are formed.

(3) A method of filling the solid acid substance on which the metal-containing catalyst composition is supported.

(4) A method of filling such that a layer of the metal-containing catalyst composition (upper-stream side) and a layer of the solid acid substance and the metal-containing catalyst composition (lower-stream side) are formed.

(5) A method of filling such that a layer of the metal-containing catalyst composition (upper-stream side) and a layer of the solid acid substance on which the metal-containing catalyst composition is supported (lower-stream side) are formed.

(6) A method of filling such that a layer of the solid acid substance and the metal-containing catalyst composition (upper-stream side) and a layer of the solid acid substance (lower-stream side) are formed.

(7) A method of filling such that a layer of the solid acid substance on which the metal-containing catalyst composition is supported (upper-stream side) and a layer of the solid acid substance (lower-stream side) are formed. The upper-stream side is an inlet side of the reactor, namely, it represents a layer that the raw materials pass through in the first half of the reaction. The lower-stream side is an outlet side of the reactor, namely, it represents a layer which is passed through in the last half of the reaction.

The reaction of the present invention may be carried out in a diluting condition by adding a solvent or gas inert to the catalyst and the reaction agents into the reaction system.

The reaction of the present invention can be carried out in any one method of batch type, semi-batch type and continuous flow type methods. It can be carried out in anyone form of liquid phase, gas phase, and gas-liquid mixed phase. As the method of filling the catalyst, it is possible to employ various methods such as fixed bed, fluid bed, suspension bed and tray fixed bed, and there is no trouble in carrying out with any method.

In carrying out the present invention, the solid acid substance and the metal-containing composition are preferably dehydrated by known methods. In the case of the fixed bed reaction method, the reactor is filled with the solid acid substance and the metal-containing composition, and should be kept at a temperature of 300° C. or higher for 10 min or more while passing an inert gas such as nitrogen and helium. Furthermore, in order to exhibit the activity of the metal-containing catalyst composition which is a hydrogenation catalyst, it is possible to carrying out treatment in a hydrogen gas stream after the dehydration treatment.

When the catalyst activity lowers at a certain elapsed time, the activities of the solid acid substance and the metal-containing composition can be recovered by carrying out reproduction with known methods.

In order to keep the production of the alkylated aromatic compound such as cumene, it is possible to employ a merry-go-round method that two or three reactors are set in parallel, and while one reactor is working for reproduction, the reaction is carried out by the remaining one or two reactors. Furthermore, when three reactors are used, it is possible to employ a method that two other reactors are connected linearly to thereby decrease the variation of the production. Moreover, when carrying out by the fluid bed flow reaction method or the moving bed reaction method, it is possible to keep the activities at a constant by taking out a part or all of the catalysts continuously or intermittently from the reactor and supplying the corresponding amount.

In the above manner, cumene can be directly obtained from by-produced acetone in the phenol production by the process of producing an alkylated aromatic compound of the present invention.

The cumene thus prepared may be utilized as a raw material for production of phenol and acetone. It can be used in a process for producing phenol comprising the following steps (a) to (d) by oxidizing the cumene and then decomposing, and further, various improved processes may be provided. The step (c) is carried out in accordance with the above process for producing an alkylated aromatic compound. The process comprises:
(a) a step of converting the cumene to by oxidization,
(b) a step of synthesizing phenol and acetone by acid-decomposing the cumene hydroperoxide,
(c) a step of synthesizing cumene by reacting the acetone generated in the step (b) with hydrogen and benzene,
(d) a step of circulating the cumene obtained in the step (c) to the step (a).

EXAMPLE

The present invention is described in more detail with reference to the examples, but the present invention is not limited by the examples.

Example 1

2.0 g of a 5% Re carbon catalyst (manufactured by NE Chemcat Co.) and 2.0 g of β zeolite (classified into 250 to 500μ after compression molding at 20 MPa, manufactured by Shokubai Kasei Co., Ltd.) were mixed homogenously, and then fed into a quartz glass reactor having a diameter of 3 cm and a length of 40 cm and calcined in a nitrogen gas stream of 30 ml/min at 500° C. for 1 hr, and then subjected to reduction treatment in a hydrogen gas stream of likewise 30 ml/min at 500° C. for 1 hr.

In the hydrogen gas stream, the temperature was decreased to 160° C., and then a mixed solution of benzene and acetone (benzene/acetone (molar ratio)=5/1) was passed through at a rate of 2.3 ml/min. A resulting product was collected by cooling an outlet.

One to two hours after the reaction start, the resulting product was analyzed by a gas chromatography. All of acetone was disappeared, and cumene, m-diisopropyl benzene and p-diisopropyl benzene were generated in amounts of 95% on the basis of the amount of acetone fed. The generation of cyclohexane was not found at all.

Example 2

1.0 g of a nickel on silica alumina catalyst (manufactured by Süd Chemie Co. G-96D, stabilized nickel, supporting amount of nickel is 59%) and 1.0 g of β zeolite were mixed homogenously, and then fed into a quartz glass reactor having a diameter of 3 cm and a length of 40 cm, and calcined in a nitrogen gas stream of 10 ml/min at 230° C. for 1 hr, and then subjected to reduction treatment in a mixed gas stream of the same nitrogen of 10 ml/min and hydrogen of 0.93 ml/min at 230° C. for 1 hr. In the nitrogen and hydrogen gas stream, the temperature was decreased to 100° C., and then a mixed solution of benzene and acetone (benzene/acetone (molar ratio)=5/1) was passed at a rate of 1.2 ml/min through the reactor. A resulting product was collected by cooling an outlet.

One to two hours after the reaction start, the resulting product was analyzed by a gas chromatography. Cumene, m-diisopropyl benzene and p-diisopropyl benzene were generated in amounts of 10% on the basis of the amount of acetone fed. The generation of cyclohexane was not found at all.

Example 3

The reaction was performed in the same manner as Example 1 except that 0.5% Pt sulfided carbon catalyst (manufactured by NE Chemcat Co.) was used in place of 2.0 g of a 5% Re carbon catalyst (manufactured by NE Chemcat Co.).

One to two hours after the reaction start, the resulting product was analyzed by a gas chromatography. Cumene, m-diisopropyl benzene and p-diisopropyl benzene were generated in amounts of 10%, and cyclohexane was generated in an amount of 6%, on the basis of the amount of acetone fed.

Example 4

The reaction was performed in the same manner as Example 1 except that Lindlar catalyst (obtainable by adding Pb to a Pd carbon catalyst manufactured by NE Chemcat Co.) was used in place of 2.0 g of a 5% Re carbon catalyst (manufactured by NE Chemcat Co.).

One to two hours after the reaction start, the resulting product was analyzed by a gas chromatography. Cumene, m-diisopropyl benzene and p-diisopropyl benzene were generated in amounts of 10%, and cyclohexane was generated in an amount of 5%, on the basis of the amount of acetone fed.

Example 5

1.0 g of a Co on alumina catalyst (manufactured by Sud Chemie Co. G-62A, supporting amount of cobalt is 40-50%) and 1.0 g of β zeolite (classified into 250 to 500μ after compression molding at 20 MPa, manufactured by Shokubai Kasei Co., Ltd.) were mixed homogenously, and then fed into a quartz glass reactor having a diameter of 3 cm and a length of 40 cm, and then treated in a nitrogen gas stream of 10 ml/min at 350° C. for 1 hr, thereafter subjected to reduction treatment in a hydrogen gas stream of the same 10 ml/min at 350° C. for 1 hr.

In the hydrogen gas stream, the temperature was decreased to 160° C., and then a mixed solution of benzene and acetone (benzene/acetone (molar ratio)=5/1) was passed through the reactor at a rate of 1.2 ml/min. A resulting product was collected by cooling an outlet.

One to two hours after the reaction start, the resulting product was analyzed by a gas chromatography. All of acetone was disappeared, and cumene, m-diisopropyl benzene and p-diisopropyl benzene were generated in amounts of 95% on the basis of the amount of acetone. The generation of cyclohexane was not found at all.

Comparative Example 1

The reaction was performed in the same manner as Example 1 except for using only a Re catalyst as a catalyst.

One to two hours after the reaction start, the resulting product was analyzed by a gas chromatography. Cumene was not generated and only isopropanol was generated.

Comparative Example 2

The reaction was performed in the same manner as Example 1 except for using only β-zeolite as a catalyst.

One to two hours after the reaction start, the resulting product was analyzed by a gas chromatography. Cumene was not generated, and only trimethyl benzene and tert-butyl benzene were generated.

Example 6

1.0 g of a 5% Re on alumina (catalyst which was prepared in accordance with Applied Catalysis A: General 162, PP. 161-169, in 1997 and whose supporting amount of Re is 5%) and 1.0 g of the β zeolite were mixed homogenously, and then fed into a quartz glass reactor having a diameter of 3 cm and a length of 40 cm and dried in a nitrogen gas stream of 30 ml/min at 350° C. for 1 hr, thereafter subjected to reduction treatment in a hydrogen gas stream of 10 ml/min at 400° C. for 3 hr.

After that, in the hydrogen gas stream of 3 ml/min, the temperature was decreased to 150° C., and then a mixed solution of benzene and acetone (benzene/acetone (molar ratio)=3/1) was passed through the reactor at a rate of 1.2 ml/min. A resulting liquid product was collected by cooling an outlet.

Furthermore, the gas collection was carried out, although it was not carried out in the above examples and comparative examples. One to three hours after the reaction start, the resulting product was analyzed by a gas chromatography (column for gas phase analysis: manufactured by VARIAN Co., PLOT FUSED SILICA 50M×0.32 MM ID COATING AL2O3/NA2SO4 DF=5 UM, column for liquid phase analysis: ZB-WAX manufactured by Phenomenex Co.). As a result, the acetone conversion rate was 97.2%, and the selectivity on the basis of acetone was, 6.5% for a hydrocarbon such as propane, 54.3% for cumene and 25.9% for diisopropyl benzene.

Example 7

The reaction and analysis were performed in the same manner as Example 6 except for using MCM-22 zeolite (obtainable by compression molding a catalyst prepared according to VERIFIED SYNTHESES OF ZEOLITIC MATERIALS Second Revised Edition 2001, P225, at 20 MPa followed by classification into 250 to 500μ) in place of β zeolite.

As a result, the acetone conversion rate was 95.6%, and the selectivity on the basis of acetone was, 7.5% for a hydrocarbon such as propane, 55.5% for cumene and 13.8% for diisopropyl benzene.

Comparative Example 3

The reaction and analysis were performed in the same manner as Example 6 except that cupper chromite (product name: G99b, element % by mass: Cu 35%, Cr 31%, Ba 2%, Mn 3%, and an atomic ratio of Zn to Cu of 0, manufactured by Süd Chemie Co.) was used in place of the 5% Re on alumina and the reduction treatment was carried out at 200° C.

As a result, the acetone conversion rate was 95.0%, and the large amounts of the hydrocarbon such as propane were by-produced such that the selectivity on the basis of acetone was, 25.1% for a hydrocarbon such as propane, 33.2% for cumene and 31.4% for diisopropyl benzene.

INDUSTRIAL APPLICABILITY

The present invention provides an industrially practical process for producing an alkylated aromatic compound in a single reaction step by directly reacting a ketone and an aromatic compound. Using the process, it is possible to obtain cumene directly from an acetone by-produced in the phenol production by the cumene method. The cumene thus obtained can be used as a raw material for production of phenol and acetone, and can be used for a process of oxidizing cumene and then decomposing it.

The invention claimed is:

1. A process for producing an alkylated aromatic compound, which process comprises reacting an aromatic compound, a ketone and hydrogen in the presence of a solid acid substance and a catalyst composition comprising at least one metal selected from the group consisting of Co, Re, Ni, Pt and Pd.

2. The process for producing an alkylated aromatic compound according to claim 1, wherein the metal is at least one metal selected from the group consisting of Co, Re and Ni.

3. The process for producing an alkylated aromatic compound according to claim 1, wherein the aromatic compound is benzene and the ketone is acetone.

4. The process for producing an alkylated aromatic compound according to claim 1, wherein the solid acid substance is a zeolite compound.

5. The process for producing an alkylated aromatic compound according to claim 1, wherein the solid acid substance is a zeolite compound having 10- to 16-membered oxygen ring pores.

6. The process for producing an alkylated aromatic compound according to claim 1, wherein the solid acid substance is a zeolite compound having 10- or 12-membered oxygen ring pores.

7. The process for producing an alkylated aromatic compound according to claim 1, wherein the solid acid substance is at least one zeolite compound selected from the group consisting of β zeolite, MCM-22 zeolite, mordenite, ZSM-5 zeolite, ZSM-12 zeolite and Y type zeolite.

8. The process for producing an alkylated aromatic compound according to claim 1, wherein the solid acid substance is at least one zeolite compound selected from the group consisting of β zeolite and MCM-22 zeolite.

9. The process for producing an alkylated aromatic compound according to claim 1, wherein the catalyst composition comprises a carrier supporting at least one metal selected from the group consisting of Co, Re, Ni, Pt and Pd.

10. The process for producing an alkylated aromatic compound according to claim 9, wherein the metal is at least one metal selected from the group consisting of Co, Re and Ni.

11. A process for producing a phenol, which process comprises:
   (a) a step of converting cumene to cumene hydroperoxide by oxidation,
   (b) a step of synthesizing phenol and acetone by acid-decomposing the cumene hydroperoxide,
   (c) a step of synthesizing cumene by reacting the acetone generated in the step (b) with hydrogen and benzene, and
   (d) a step of circulating the cumene obtained in the step (c) to the step (a), wherein the step (c) is carried out in accordance with the process as claimed in claim 1.

12. The process for producing an alkylated aromatic compound according to claim 9, wherein the carrier is at least one carrier selected from silica, alumina, silica alumina, titania, magnesia, silica magnesia, zirconia, carbon, acid clay and diatomaceous earth.

\* \* \* \* \*